United States Patent
Reif et al.

(10) Patent No.: US 9,480,828 B2
(45) Date of Patent: Nov. 1, 2016

(54) TREATMENT METHOD FOR THE INFERIOR TURBINATE

(71) Applicant: GYRUS ACMI, INC., Southborough, MA (US)

(72) Inventors: Matthias Reif, Philadelphia, PA (US); John Flynn, Jr., Collierville, TN (US); Chris Olig, Eden Prairie, MN (US); Rod Schlossor, Mt. Pleasant, SC (US); Ben Bleir, Boston, MA (US); Alex Chiu, Tucson, AZ (US)

(73) Assignee: GYRUS ACMI, INC., Southborough, MA (US)

( * ) Notice: Subject to any disclaimer, the term of this patent is extended or adjusted under 35 U.S.C. 154(b) by 75 days.

(21) Appl. No.: 14/528,525

(22) Filed: Oct. 30, 2014

(65) Prior Publication Data

US 2015/0133851 A1 May 14, 2015

Related U.S. Application Data (60) Provisional application No. 61/904,103, filed on Nov. 14, 2013.

(51) Int. Cl.
*A61M 31/00* (2006.01)
*A61L 31/16* (2006.01)
*A61L 31/14* (2006.01)
*A61L 31/04* (2006.01)
(Continued)

(52) U.S. Cl.
CPC ............ *A61M 31/002* (2013.01); *A61B 17/24* (2013.01); *A61K 9/0043* (2013.01); *A61K 47/36* (2013.01); *A61M 37/0069* (2013.01); *A61B 17/32002* (2013.01); *A61B 18/1485* (2013.01); *A61B 2018/00601* (2013.01); *A61M 2205/04* (2013.01)

(58) Field of Classification Search
CPC ................... A61B 17/32053; A61B 18/1485; A61B 2017/320056; A61B 2018/00601; A61L 31/042; A61L 31/148; A61L 31/16; A61M 2205/04; A61M 31/002; A61M 31/00
See application file for complete search history.

(56) References Cited

U.S. PATENT DOCUMENTS

| 6,432,126 B1 * | 8/2002 | Gambale | A61F 2/2493 623/1.1 |
| 7,361,168 B2 * | 4/2008 | Makower | A61B 5/06 604/509 |

(Continued)

FOREIGN PATENT DOCUMENTS

| WO | 2005/079749 A2 | 9/2005 |
| WO | 2009/132226 A1 | 10/2009 |

OTHER PUBLICATIONS http://www.medicinenet.com/sinusitis_pictures_slideshow/article. htm Last Accessed Sep. 30, 2013. Material last reviewed John P. Cunha, DO FACOEP on Jun. 20, 2013, 15 5lides.

(Continued)

*Primary Examiner* — Quynh-Nhu H Vu
(74) *Attorney, Agent, or Firm* — The Dobrusin Law Firm, P.C.

(57) ABSTRACT

Disclosed is a method comprising: creating one or more pockets within an inferior turbinate of a patient, inserting one or more it that are easily inserted into the one or more pockets, wherein the one or more implants contain one or more therapeutic compounds and the one or more implants do not need to be removed from the inferior turbinate after implantation into the one or more pockets.

17 Claims, 5 Drawing Sheets

(51) Int. Cl.
*A61M 37/00* (2006.01)
*A61K 9/00* (2006.01)
*A61K 47/36* (2006.01)
*A61B 17/24* (2006.01)
*A61B 18/00* (2006.01)
*A61B 18/14* (2006.01)
*A61B 17/32* (2006.01)

(56) References Cited

U.S. PATENT DOCUMENTS

| | | | |
|---|---|---|---|
| 7,544,192 B2 | 6/2009 | Eaton et al. | |
| 7,662,141 B2 | 2/2010 | Eaton et al. | |
| 7,662,142 B2 | 2/2010 | Eaton et al. | |
| 7,686,798 B2 | 3/2010 | Eaton et al. | |
| 7,691,094 B2 | 4/2010 | Eaton et al. | |
| 7,713,255 B2 | 5/2010 | Eaton et al. | |
| 7,951,130 B2 | 5/2011 | Eaton et al. | |
| 7,951,131 B2 | 5/2011 | Eaton et al. | |
| 7,951,132 B2 | 5/2011 | Eaton et al. | |
| 7,951,133 B2 | 5/2011 | Eaton et al. | |
| 7,951,134 B2 | 5/2011 | Eaton et al. | |
| 7,951,135 B2 | 5/2011 | Eaton et al. | |
| 8,109,918 B2 | 2/2012 | Eaton et al. | |
| 2002/0182186 A1* | 12/2002 | Loeb | 424/93.7 |
| 2006/0067982 A1* | 3/2006 | Haapakumpu | A61K 9/0043 424/434 |
| 2008/0077240 A1* | 3/2008 | Saidi | A61F 2/18 623/10 |
| 2008/0097380 A1* | 4/2008 | Li | 604/506 |
| 2008/0194544 A1 | 8/2008 | Krishnamoorthy | |
| 2008/0248991 A1 | 10/2008 | Dyer et al. | |
| 2009/0030409 A1* | 1/2009 | Goldfarb | A61M 25/01 606/14 |
| 2009/0269417 A1* | 10/2009 | Gonzalez | A61K 9/0019 424/616 |
| 2009/0270346 A1 | 10/2009 | Tijsma et al. | |
| 2009/0298792 A1* | 12/2009 | Grassauer et al. | 514/55 |
| 2010/0121141 A1* | 5/2010 | Rontal | A61B 1/0051 600/106 |
| 2010/0291055 A1 | 11/2010 | Athanasiadis et al. | |
| 2013/0174849 A1* | 7/2013 | Atkinson | A61M 15/08 128/206.11 |
| 2013/0211194 A1* | 8/2013 | Guyton et al. | 600/37 |
| 2015/0100133 A1* | 4/2015 | Xie | A61F 2/90 623/23.7 |

OTHER PUBLICATIONS

Olympus, *DIEGO PKSMR Application Guide* Jun. 2011.
"Sinusitis Pictures Slideshow: Symptoms, Diagnosis, Treatment" MedicineNet.com, Jun. 20, 2013.

* cited by examiner

TREATMENT METHOD FOR THE INFERIOR TURBINATE

This application claims the benefit of U.S. Provisional Application No. 61/904,103, filed Nov. 14, 2013, the entire contents of which are herein incorporated by reference.

FIELD

The present disclosure relates to a method for the creation of one or more pockets within an inferior turbinate of the nasal passage and the insertion of an implant containing one or more therapeutic compounds, into the one or more pockets of the inferior turbinate of a patient to treat nasal related problems.

BACKGROUND

Individuals who suffer from rhinitis are all too familiar with its unpleasant symptoms. The common symptoms of rhinitis include stuffy nose, sneezing, runny nose, and post nasal drip. Sufferers of rhinitis often seek relief from over the counter treatments. However, when over the counter treatments fail, many rhinitis sufferers end up seeking further relief from their physician. Doctors currently have a limited number of options for providing relief to patients. For most individuals the current treatments are oral drugs and nasal sprays, see U.S. 2008/0194544A1, incorporated herein by reference in its entirety. Oral drugs take time to start working since they have to be broken down by the body, and then enter the blood stream before they can begin to work. Nasal sprays deliver the medicine in a more direct way than oral drugs, for the medicine is sprayed directly into the nasal passage. Although nasal sprays are sprayed into the nasal passage where the medicine ends up is random and relief of symptoms may not be consistent.

The direct application of medicine or a therapeutic compound to the affected tissue has been found to provide the best opportunity to reduce symptoms. It has also been found that the longer therapeutic compounds are maintained in the body, the better the results. Pharmaceutical compositions have been developed that allow for the uptake of therapeutic compounds across the mucosal surface. These compositions contain plasticizers, chitosan derivatives and therapeutic compounds for use in a gel that when applied to a mucosal surface can be absorbed by the body, see WO 2005/079749 incorporated herein by reference in its entirety. Another means for direct application of a therapeutic compound that has been developed is a delivery device, see U.S. Pat. No. 7,361,168, incorporated herein by reference in its entirety. The delivery device is loaded with a desired substance then implanted into the body. The delivery device then controls the rate that the substance is released into the body.

In severe cases of rhinitis it may be decided that sinus surgery is the best course of action. Sinus surgery is performed to remove excess tissue from the nasal cavities. The removal of excess tissue helps to relieve the symptoms experienced by rhinitis suffers.

A hydrogel containing chitosan has been developed to assist in the healing process. The gel may be placed on the area which has been resected, see U.S. 2010/0291055, incorporated herein by reference in its entirety. Gels have also been developed that are biodegradable, biocompatible or bioabsorbable allowing for easy absorption into the body and faster localized healing, see WO 2009/132226, incorporated herein by reference in its entirety. The steroids that are currently available for the application within the nose are designed to be applied on the surface of the mucosal tissue and are not able to remain on the tissue for long periods of time. A method for applying a long lasting, effective therapeutic compound within the nose to relieve and prevent rhinitis symptoms is needed.

What is also needed is a method which combines pharmaceutical and surgical approaches for relieving the rhinitis symptoms and preventing further symptoms from arising for an extended period of time without the need of a systematic drug regimen. What is also needed is a method for implanting a long lasting, effective therapeutic compound in the nose which can be done in an office setting. What is also needed is a long lasting effective nasal implant with a therapeutic compound, which does not need to be removed.

SUMMARY

The present invention seeks to address one or more of these problems by providing a method which uses both pharmaceutical and surgical approaches to create a directly applied implant within the nose to provide a on lasting, effective delivery of one or more therapeutic compounds to treat and/or prevent rhinitis symptoms. This method may be used in an office setting or an operating room depending on the severity of swelling within the nose and/or other comorbidities.

In an embodiment, the invention provides a method of creating one or more pockets within an inferior turbinate of a patient, and inserting one or more implants into the one or more pockets, wherein the one or more implants contain one or more therapeutic compounds. The one or more implants do not need to be removed from the inferior turbinate after implantation into the one or more pockets. In some embodiments, the one or more inserted implants are biodegraded over a period of time in the body of the patient, rendering a removal process/procedure unnecessary. In some embodiments, the one or more inserted implants are biodegraded in about 14 days or more. In some embodiments, the one or more inserted implants are biodegraded in about 30 or more days. In some embodiments, the invention provides a method of creating one or more pockets within an inferior turbinate of a patient, and inserting one or more implants into the one or more pockets of the inferior turbinate, wherein the one or more implants further comprise a biomaterial that contains one or more therapeutic compounds that elute into a body wherein the one or more implants do not need to be removed from the inferior turbinate after implantation into the one or more pockets. In some embodiments, the one or more inserted implants are biodegraded over a period of time in the body of the patient, rendering a removal process/procedure unnecessary. In some embodiments, the one or more inserted implants are biodegraded in about 14 days or more. In some embodiments, the one or more inserted implants are biodegraded in about 30 or more days.

In some embodiments of the invention, the one or more pockets may be created during endoscopic sinus surgery under direct visualization. In some embodiments of the invention, the one or more pockets may be created by a debrider instrument or an electrical energy instrument. In some embodiments of the invention, the one or more pockets may be created by a bipolar submucosal resection instrument or a radio frequency instrument.

In some embodiments of the invention, an insertion instrument may be used to insert the one or more implants into the one or more pockets. In some embodiments of the invention, the insertion instrument may be a debrider instrument or electrical energy instrument.

In some embodiments of the invention, the one or more implants each comprise a biomaterial that can bind with the one or more therapeutic compounds. In some embodiments, the biomaterial is capable of holding together the one or more therapeutic compounds in the one or more implants. In some embodiments of the invention, the one or more therapeutic compounds elute into the body of the patient.

In some embodiments of the invention, the biomaterial breaks down over a known period of time to allow the body to absorb and metabolize the therapeutic compound. In another embodiment of the invention, the biomaterial reduces adhesion formation, promotes healing, and/or reduces tissue inflammation. In some embodiments of the invention, the therapeutic compound is a steroid. In some embodiments of the invention, the therapeutic compound contains an anti-inflammatory carbohydrate polymer. In some embodiments of the invention, the therapeutic compound is an anti-inflammatory carbohydrate polymer with a steroid.

Until the present invention the majority of rhinitis suffers were left with pharmaceutical treatments which provide temporary relief of symptoms and require a systemic drug treatment. It was only in extenuating circumstances that surgery was even considered an option. The present invention combines pharmaceutical and surgical approaches to relieve and prevent rhinitis symptoms. The present invention also provides an effective treatment by delivering a long lasting, effective steroid to the source of the problem. The present invention may be implemented in an office setting and does not require a follow-up appointment to remove the implant.

DETAILED DESCRIPTION

The explanations and illustrations presented herein are intended to acquaint others skilled in the art with the invention, its principles, and its practical applications. Those skilled in the art may adapt and apply the invention in its numerous forms, as may be best suited to the requirements of a particular use. The specific embodiments of the present invention as set forth are not intended as being exhaustive or limiting of the invention. The scope of the invention should be determined not with reference to the above description, but should be determined with reference to the appended claims, along with the full scope of equivalents to which such claims are entitled. Other combinations are also possible as will be gleaned from the following claims, which are hereby incorporated by reference into this written description.

The method disclosed herein comprises creating one or more pockets within a nose, preferably the inferior turbinate of a patient, and then inserting one or more implants that may be easily inserted into the one or more pockets. The implants contain one or more therapeutic compounds and do not need to be removed after insertion. The inserted implants are biodegraded over a period of time without a need for a later removal process or procedure. The one or more pockets may be created in an area of the nose where there is an excess of tissue. Preferably the one or more pockets are created in the inferior turbinate. The one or more pockets may be created during endoscopic sinus surgery. This allows doctors to use precision when removing excess tissue from the nose. A debrider instrument or an electrical energy instrument may be used in endoscopic sinus surgery to create the one or more pockets.

The nose has three pairs of turbinates on either side of the septum, the superior, middle and inferior. The turbinates play a role in the respiratory system, immune system and olfaction. The inferior turbinate is the largest and lowest of the three turbinates. The inferior turbinate is comprised of mucosal tissue and bone. The inferior turbinate is the first line of defense for human body against airborne irritants. Rhinitis symptoms often result from the irritation of this area. The one or more pockets are preferably created within the inferior turbinates. The one or more pockets may be created within the inferior turbinate on either side of the septum. Both inferior turbinates may undergo reduction during a single procedure depending on the needs of the patient. One or more pockets may be created in the inferior turbinate with the greatest amount of hypertrophy.

In some embodiments of the invention, a debrider instrument may be used to create the one or more pockets. A debrider instrument has the ability to remove tissue and bone. A debrider instrument has two or more types of activation which may be used during its use. One possible type of activation for a debrider instrument is the use of bipolar energy. Another possible type of activation for the debrider instrument is motorized dissection.

An opening in the inferior turbinate may be created to allow the debrider instrument easier access inside of the inferior turbinate. In some embodiments of the invention where a debrider instrument is used, the debrider blade is used to create an opening in the inferior turbinate. To use the debrider blade to create the opening, the debrider blade is oriented laterally away from the septum and then lightly pushed into the tissue. The debrider may then be activated to create a smooth hemostatic entry through the soft tissue towards the turbinate bone. Preferably, bipolar energy is used to activate the debrider blade when creating the entry into the inferior turbinate. After the creation of a smooth hemostatic entry motorized dissection may be used allowing the debrider blade to undermine the mucosa.

In some other embodiments of the invention where a debrider instrument is used, an incision is made prior to the entry of the debrider into the inferior turbinate. The debrider blade used may be any blade which is capable of forming an appropriately sized incision. In some embodiments of the invention where an incision is first made, a number 15 blade or similar instrument is used to make a stab incision in the anterior head of the inferior turbinate. Following the creation of the stab incision a submucosal opening may be created within the inferior turbinate. Preferably the opening is created along the medial surface of the turbinate bone, using an instrument suitable to create an appropriate sized opening, for example a Cottle elevator. The debrider instrument is then placed into the opening of the inferior turbinate so that the debrider blade is oriented inferolaterally. The debrider instrument is then inserted into the inferior turbinate, where excess tissue and bone may be continuously removed in an anterior to posterior direction along the length of the inferior turbinate. In one embodiment of the invention, the debrider blade may be rotated within the inferior turbinate to address areas where there is tissue hypertrophy. Preferably a nose cone of the debrider is used to position the debrider to best address the areas of tissue hypertrophy. More preferably a DIEGO® or DIEGO ELITE™ nose cone is used to address the areas of tissue hypertrophy. During the removal of tissue two or more types of activation may be used together. Preferably motorized dissection and bipolar energy are the activation forms used. Preferably the debrider instrument is a bipolar submucosal resection instrument, or a bipolar turbinate blade, or the like. An example of a bipolar resection instrument on the market is the DIEGO® submucosal resection instrument by Olympus. An example of a bipolar turbinate blade is the DIEGO ELITE™ bipolar turbinate blade. One or more implants are inserted into the one or more pockets that have been created by the debrider instrument.

In some other embodiments of the invention, an electrical energy instrument may be used to create the one or more pockets. An electrical energy instrument may be used on tissue. An electrical energy instrument has a probe that is inserted into the inferior turbinate. The probe is inserted into the inferior turbinate and positioned to create the one or more pockets starting from the posterior end. The pocket is created when tiny lesions are created by the probe within the tissue. Following the creation of a pocket one or more implants are inserted into the pocket. The probe is then moved slightly toward the anterior end of the inferior turbinate, where another pocket may be created. An implant is then inserted into the newly created pocket. This process is repeated until the desired number of pockets has been created and implants inserted into the one or more pockets. Preferably the electrical energy instrument used in the invention is a radio frequency induced thermotherapy instrument (RFiTT) or the like. An example of an RFiTT on the market is a CELON PRO BREATH™ instrument by Olympus.

One or more implants may be implanted into the one or more pockets created during endoscopic sinus surgery. Preferably an implant comprises a biocompatible carrier, for example a gel, hydrogel, foam, powder, wafer, capsule, cartridge, aqueous solution, aqueous composition, biocompatible polymer, biocompatible copolymer, or the like, or any combination thereof. More preferably the implant is a gel, hydrogel, capsule, cartridge, biocompatible polymer, biocompatible copolymer, or the like, or any combination thereof. Most preferably the implant is a gel, hydrogel, cartridge, biocompatible polymer, biocompatible copolymer, or the like, or any combination thereof. In some embodiments of the invention, the implant may change viscosity, upon implantation. In some embodiments of the invention, the implant requiref the addition of an aqueous solution to be effective. In some embodiments of the invention, the implant may be prepared for insertion by mixing a solid form with an aqueous solution prior to being inserted.

In some embodiments of the invention, the implant contains one or more therapeutic compounds. The one or more therapeutic compounds elute into the body. The one or more therapeutic compounds may be any substance that can be used to prevent or treat a condition or disease in the body. Preferably the therapeutic compound includes anti-inflammatory carbohydrate polymers, steroids, analgesics, antibiotics, antihistamines, vaso-constrictors, the like, or any combination thereof. More preferably the therapeutic compound includes anti-inflammatory carbohydrate polymers, steroids, analgesics, antihistamines, the like, or any combination thereof. Most preferably the therapeutic compound includes anti-inflammatory carbohydrate polymers, steroids, antihistamines, the like, or any combination thereof.

In some embodiments of the invention, the implant may be a biomaterial that serves as a vehicle within the body to deliver one or more therapeutic compounds across a mucosal surface. Preferably, the biomaterial can bind with the one or more therapeutic compounds. In some embodiments of the invention, the biomaterial breaks down over a known period of time to allow the body to absorb and metabolize the one or more therapeutic compounds. Preferably the biomaterial breaks down over about 14 days or more. Most preferably the biomaterial breaks down over about 30 days or more. In some embodiments of the invention, the biomaterial reduces adhesion formation. Preferably the biomaterial used is chitosan, a chitin based polymer sponge, co-polymer urethane, carboxy methyl cellulose, esterified hyaluronic acid with bovine collagen, plant based polymer sponge, or the like. More preferably the biomaterial is chitosan, a chitin based polymer sponge, plant based polymer sponge, or the like. Most preferably the biomaterial is chitosan, or the like. In some embodiments, the biomaterial is chitosan based. In some embodiments, the chitosan based biomaterial breaks down in the body of the patient in about 14 days or more. In some embodiments, the chitosan based biomaterial breaks down in the body of the patient in about 30 days or more.

In some embodiments of the invention, the implant may be hydrogel based. In some embodiment, the implant may be a chitosan based. The implants can be made based on the known methods such as described in U.S. 2010/0291055 and WO 2009/132226. In some embodiments, the implant may be hydrogel based further containing a therapeutic compound. In some embodiments, the implant may be chitosan based polymer sponge further containing a therapeutic compound. In some embodiments, the implant may be chitosan based polymer sponge further containing a steroid. In some embodiments, the implant may be chitosan based polymer sponge further containing an anti-inflammatory agent, or an analgesic, or an antibiotic, or an antihistamine. In some embodiments, the inserted implant may be biodegraded over a period of time in the body of the patient. In some embodiments, the inserted implant may be degraded in about 14 days or more. In some embodiments, the inserted implant may be degraded in about 30 days or more.

In some embodiments of the invention, the one or more implants may be inserted into the inferior turbinate using one or more techniques. Preferably the one or more techniques involve an insertion instrument, a debrider instrument, or an electrical energy instrument. An insertion instrument may be used to insert the implant into the inferior turbinate. An insertion instrument is any suitable instrument for placing the implant into the inferior turbinate and may be dependent on the physical characteristics of the implant. The one or more implants may be inserted using the debrider instrument without the debrider instrument being removed from the nasal cavity after the one or more pockets have been created. When the resection of tissue is complete the one or more implants may be inserted through the catheter within the debrider instrument. The one or more implants may also be inserted through an implant instrument that is part of the debrider instrument. In some embodiments of the invention, the debrider instrument is removed from the inferior turbinate to place the one or more implants into the debrider instrument. The debrider instrument is then placed back into the inferior turbinate to insert the one or more implants. In another embodiment of the invention, the one or more implants may be inserted using the electrical energy instrument that is designed to insert the implant. The electrical energy instrument used to insert the implant has a center similar to a hypodermic needle allowing for the injection of the one or more implants into the one or more pockets without the electrical energy instrument being removed. A patient's needs, and the physical characteristics of the implant will determine the one or more techniques used to insert the one or more implants.

The following description of the figures is provided to aid in an understanding of the claimed invention. The description is not meant to limit the scope of the claims to which the inventors are entitled.

Figure 1:
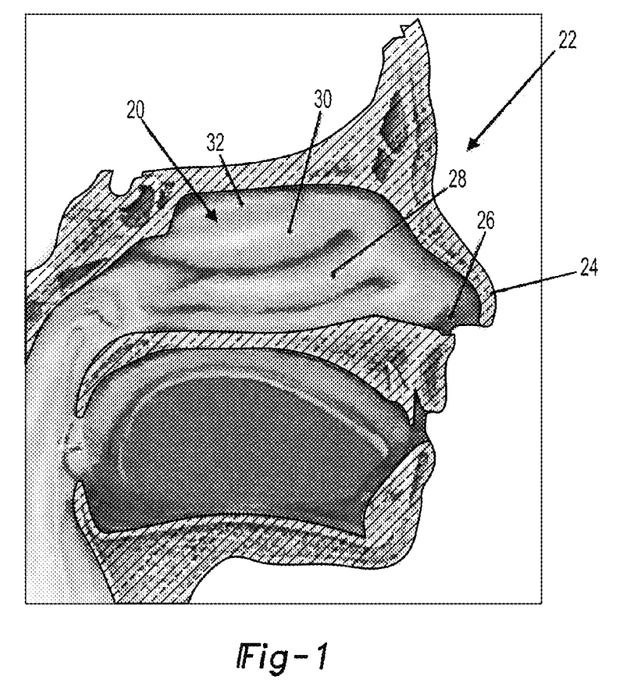
FIG. 1 is a cross sectional view of the nasal cavity in a human body.

FIG. 1 shows a cross sectional view of the nasal cavity 20 of the human body 22 with the septum (not shown in FIG. 1) removed. The nasal cavity 20 is divided by the septum (not shown in FIG. 1) and has two sides. Each side has three turbinates. When entering the nasal cavity 20 from the outside of the nose 24 through the nostril 26 the first turbinate is the inferior turbinate 28 which is the longest of the three. Above the inferior turbinate 28 is the middle turbinate 30, and above both of them is the superior turbinate 32.

Figure 2:
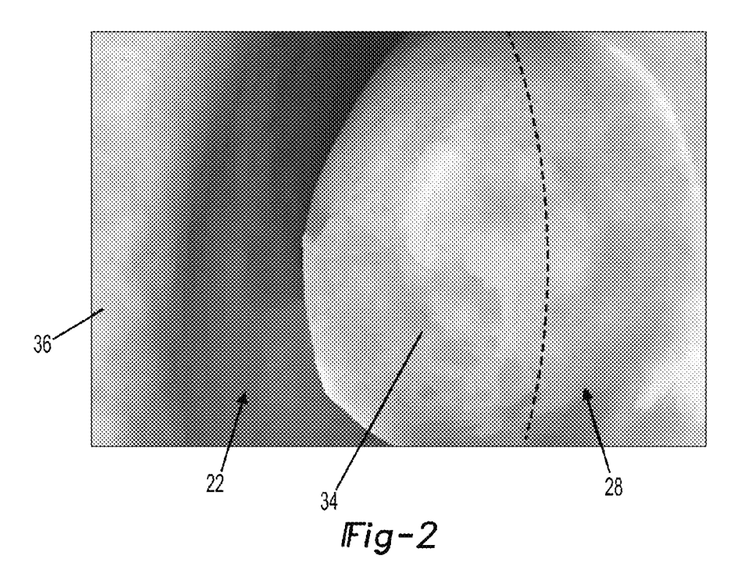
FIG. 2 is the exterior of the anterior wall of an inferior turbinate prior to the creation of one or more pockets.

FIG. 2 is an illustration of a left nasal cavity 22 with an inferior turbinate 28 that has hypertrophic tissue 34. It is important to note that hypertrophic tissue can occur in the inferior turbinate on either side of the septum 36.

Figure 3:
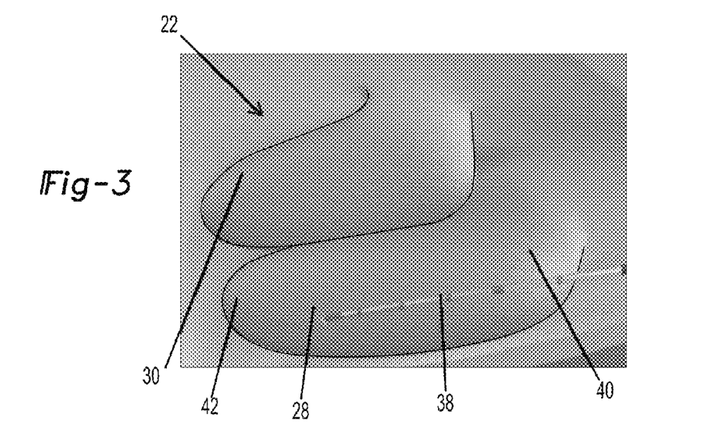
FIG. 3 is an illustration of an electrical energy instrument within the inferior turbinate.

FIG. 3 is an illustration of an embodiment of the invention where an electrical energy instrument 38 is inserted into the inferior turbinate 28 at its anterior end 40 then inserted further towards the posterior end 42 where it can begin to create the one or more pockets 44 (not shown in FIG. 3).

Figure 4:
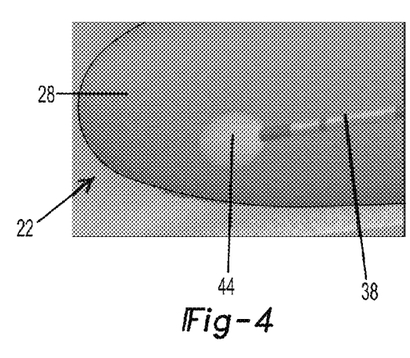
FIG. 4 is an illustration of an embodiment of the invention where an electrical energy instrument is used to create pockets within the inferior turbinate.

FIG. 4 is an illustration of an embodiment of the invention where the electrical energy instrument 38 that has been inserted into the inferior turbinate 28 as illustrated in FIG. 3 creates one or more pockets 44.

Figure 5:
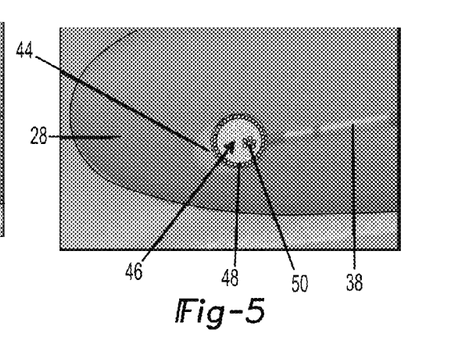
FIG. 5 is an embodiment of the invention illustrating a therapeutic compound being injected into a pocket.
Figure 6:
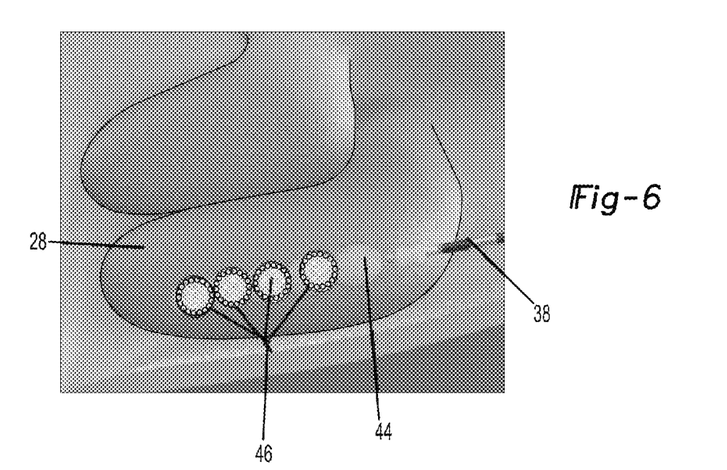
FIG. 6 is an embodiment of the invention illustrating the creation of pockets from the Posterior to Anterior ends of the inferior turbinate and the injection of a therapeutic compound into the pockets.

FIG. 5 and FIG. 6 are illustrations of some embodiments of the invention where after the electrical energy instrument 38 creates one or more pockets 44, one or more implants 46 are inserted into the one or more pockets 44 using the electrical energy instrument 38. In this embodiment the one or more implants 46 are inserted following the creation of the one or more pockets 44. The implants 46 contain one or more therapeutic compounds 48 and a biomaterial 50.

Figure 7:
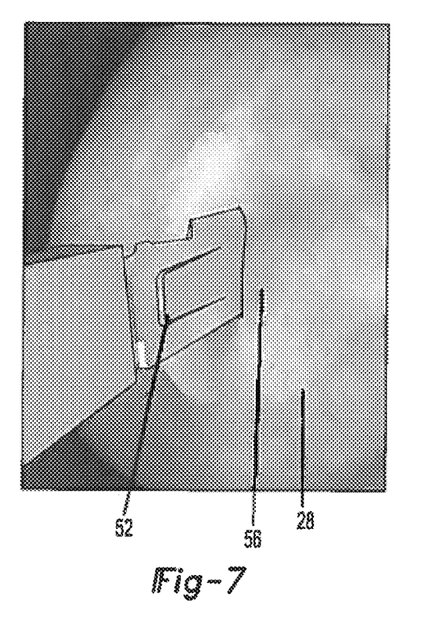
FIG. 7 is an illustration of an embodiment of the invention where a blade is used to create an incision in the inferior turbinate.
Figure 8:
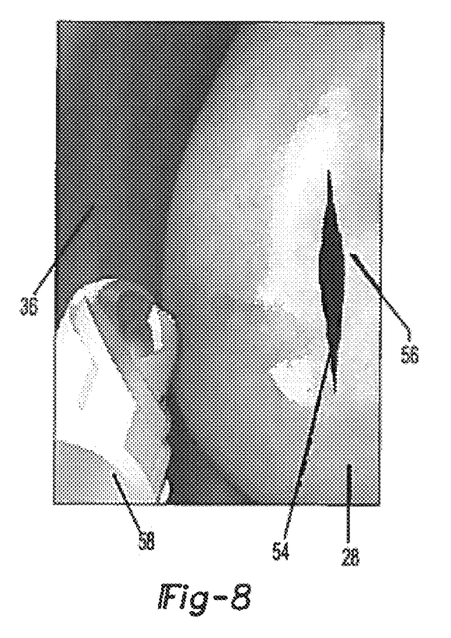
FIG. 8 is an illustration of an embodiment of the invention where a debrider enters the inferior turbinate through the incision created by the blade in FIG. 7.

FIG. 7 and FIG. 8 are illustrations of an embodiment of the invention where a blade 52 is used to create an incision 54 in the anterior head 56 of the inferior turbinate 28 to allow the debrider instrument 58 to enter the inferior turbinate 28.

Figure 9:
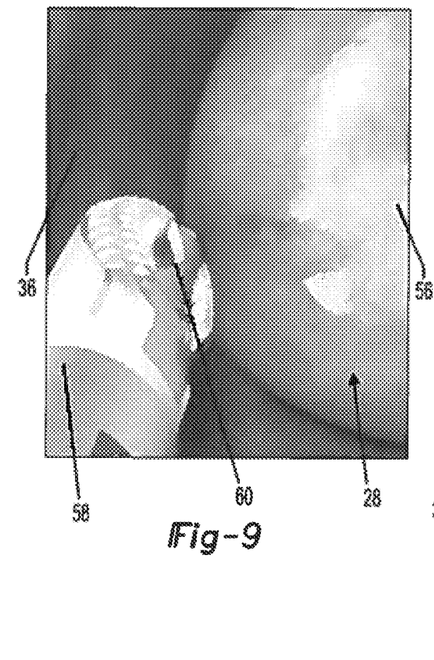
FIG. 9 is an illustration of an embodiment of the invention where the debrider blade is used to create an incision in the inferior turbinate.
Figure 10:
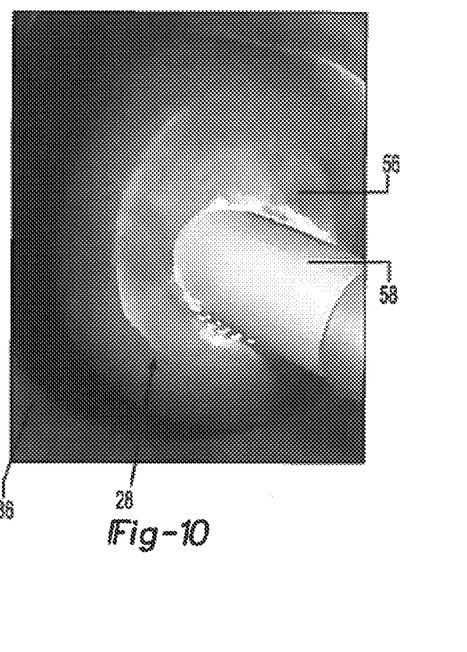
FIG. 10 is an illustration of an embodiment of the invention where the debrider instrument continues into the inferior turbinate after the debrider blade creates an incision.

FIG. 9 and FIG. 10 show an alternative embodiment of the invention where the debrider instrument 58 having a debrider blade 60 may be used to create a hemostatic entry into the inferior turbinate 28 from the anterior head 56 of the inferior turbinate 28. To make the hemostatic entry the debrider instrument 58 is turned so that the debrider blade 60 is facing down and away from the septum 36.

Figure 11:
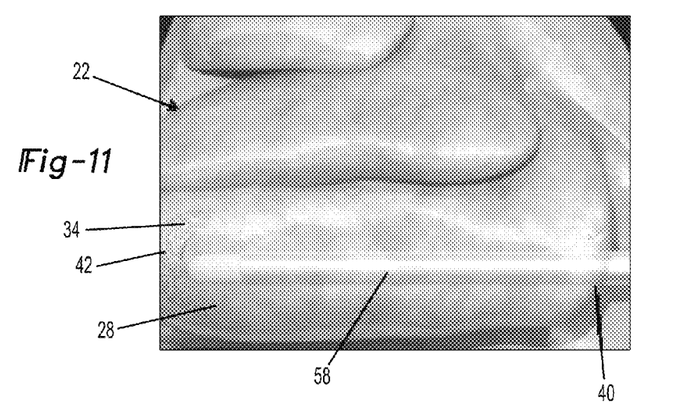
FIG. 11 is an illustration of an embodiment of the invention where a debrider instrument creates a submucosal tunnel as it works its way to the posterior end of the inferior turbinate, to then create a pocket from the posterior to anterior end in inferior turbinate.

FIG. 11 shows an embodiment of the invention where the debrider instrument 58 is inserted into the inferior turbinate 28 at the anterior end 40 of the inferior turbinate 28. The debrider instrument then removes hypertrophic tissue 34 as it moves towards the posterior end 42.

Figure 12:
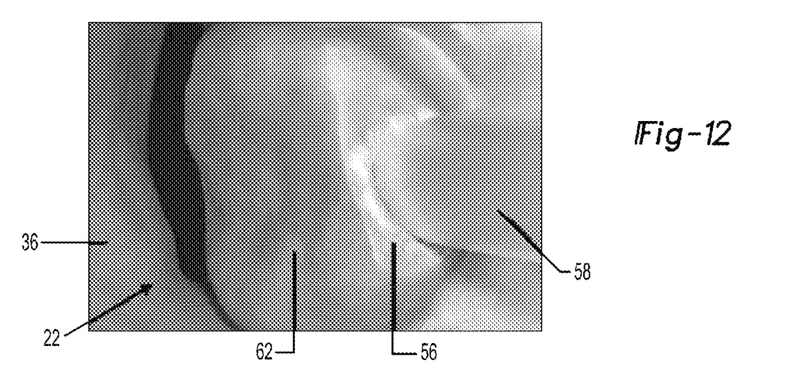
FIG. 12 is the exterior of the anterior wall of an inferior turbinate following the creation of one or more pockets.

FIG. 12 is an illustration of an embodiment of a reduced inferior turbinate 62 after the hypertrophic tissue 34 has been removed by a debrider instrument 58.

Figure 13:
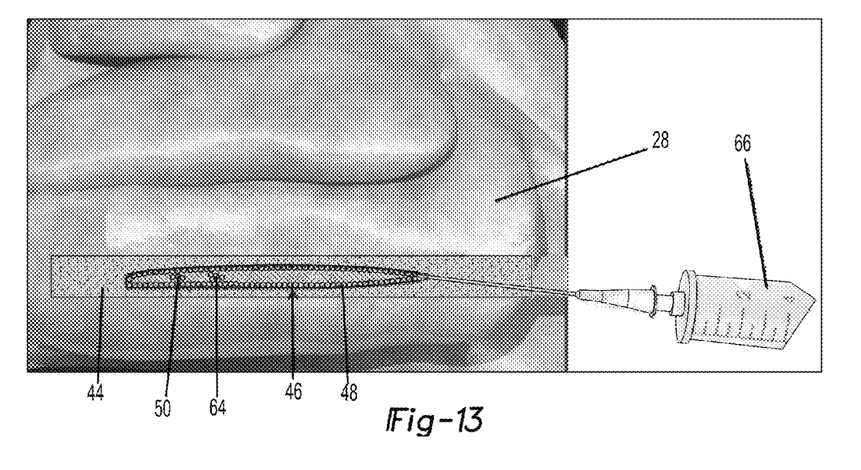
FIG. 13 is an illustration of an embodiment of the invention where a therapeutic compound is injected into the pocket as created in FIG. 11.
Figure 14:
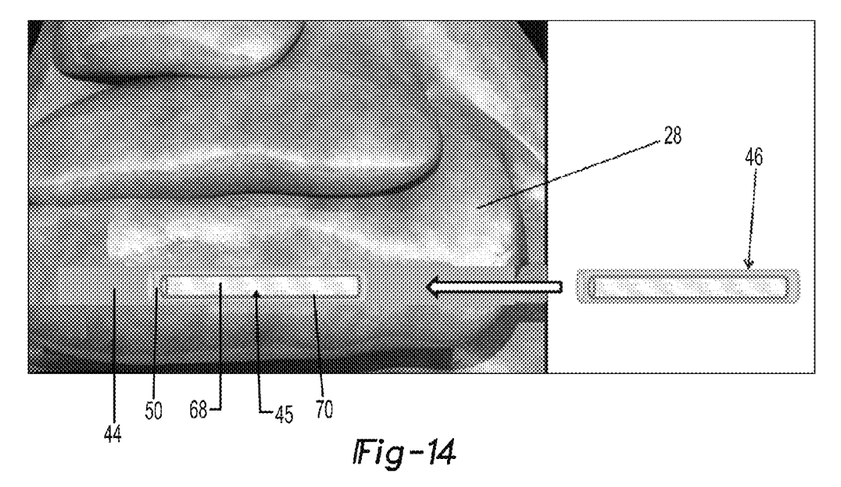
FIG. 14 is an illustration of another embodiment of the invention where a therapeutic implant is inserted into the pocket as created in FIG. 11.

FIG. 13 and FIG. 14 show an embodiment of the invention where one or more implants 46 are inserted into the one or more pockets 44 that have been created by the debrider instrument 58 (not shown in FIG. 13 or FIG. 14). In FIG. 13 the one or more implants 46 have a biomaterial 50 and one or more therapeutic compounds 48 such as an anti-inflammatory carbohydrate polymer with a steroid 64 and is inserted by an insertion instrument 66. In FIG. 14 the one or more implants 46 have a biomaterial 56 and one or more therapeutic compounds 48, such as an anti-inflammatory carbohydrate polymer 68 and a steroid 70.

Figures 15, 16:
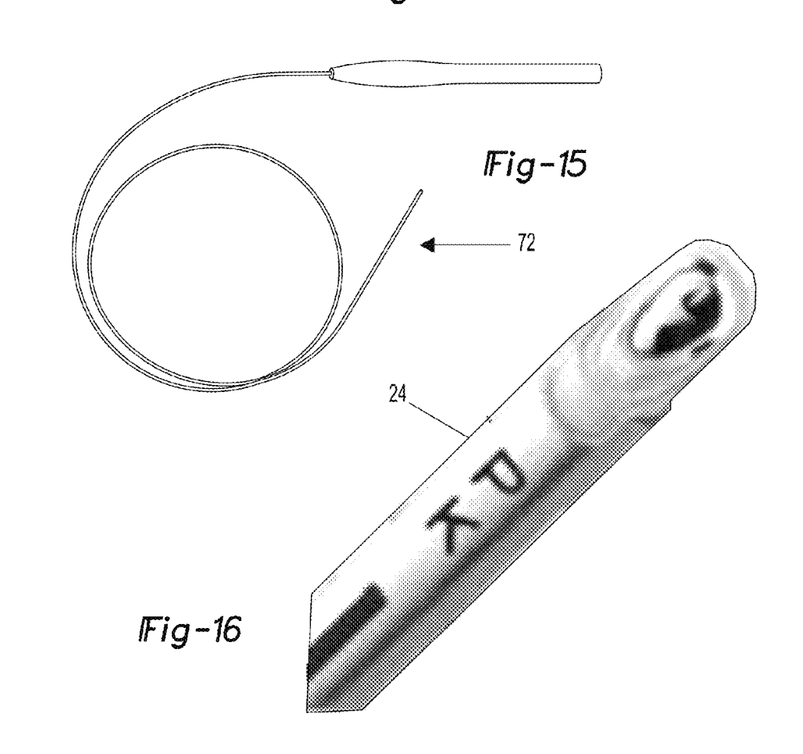
FIG. 15 is an illustration of a radio frequency instrument
FIG. 16 is an illustration of a bipolar submucosal resection instrument.

FIG. 15 is an embodiment of an electrical energy instrument 38 or in this figure a Radio Frequency instrument 72.

FIG. 16 is an embodiment of a debrider instrument 58 or in this figure a bipolar submucosal resection instrument 74.

What is claimed:

1. A method comprising:
   a) creating one or more pockets sufficiently large to completely enclose one or more implants within an inferior turbinate of a patient, wherein the one or more pockets are created by a debrider instrument or an electrical energy instrument; and
   b) inserting the one or more implants into the one or more pockets with the debrider instrument or the electrical energy instrument after the one or more or more pockets are created, wherein the one or more implants contain one or more therapeutic compounds.

2. The method of claim 1, wherein the one or more pockets are created during sinus surgery under direct visualization.

3. The method of claim 1, wherein the one or more pockets are created by a bipolar submucosal resection instrument or a radio frequency instrument.

4. The method of claim 1, wherein the one or more implants are degraded over a period of time in the body of the patient.

5. The method of claim 1, wherein the one or more implants further comprise a biomaterial that can bind with the one or more therapeutic compounds.

6. The method of claim 5 wherein the biomaterial breaks down over a period of time to allow absorption and metabolization of the one or more therapeutic compounds.

7. The method of claim 5, wherein the biomaterial is chitosan based hydrogel.

8. The method of claim 1, wherein the therapeutic compound is a steroid.

9. The method of claim 1, wherein the therapeutic compound is an anti-inflammatory carbohydrate polymer.

10. The method of claim 1, wherein the therapeutic compound is an anti-inflammatory carbohydrate polymer with a steroid.

11. The method of claim 1, wherein the debrider instrument is used to insert the one or more implants without removing the debrider instrument from a nasal cavity after the one or more pockets have been created.

12. The method of claim 11, wherein the debrider instrument includes a catheter and the one or more implants are inserted through the catheter.

13. The method of claim 1, wherein the electrical energy instrument is used to insert the one or more implants without removing the electrical energy instrument from a nasal cavity, and the electrical energy instrument includes a center needle through which the one or more implants are injected into the one or more pockets.

14. A method comprising:
a) creating one or more pockets within an inferior turbinate of a patient, wherein the one or more pockets are created by a debrider instrument or an electrical energy instrument; and
b) inserting one or more implants into the one or more pockets with the debrider instrument or the electrical instrument, wherein the one or more implants comprise a biomaterial that contains one or more therapeutic compounds, and wherein the one or more implants do not need to be removed from the inferior turbinate after implantation into the one or more pockets.

15. The method of claim 14 wherein the one or more pockets are created during endoscopic sinus surgery.

16. The method of claim 14, wherein the one or more pockets are created by a bipolar submucosal resection instrument or a radio frequency instrument.

17. A method of treating rhinitis of a patient, comprising:
a) creating one or more pockets sufficiently large to completely enclose one or more implant within an inferior turbinate of the patient, wherein the one or more pockets are created by a debrider instrument or an electrical energy instrument; and
b) inserting the one or more implants into the one or more pockets with the debrider instrument or the electrical energy instrument after the one or more pockets are created, wherein each of the one or more implants comprises a biomaterial that contains one or more therapeutic compounds, and wherein the one or more implants are degraded over a period of time in the body of the patient.

* * * * *